US008921327B2

(12) United States Patent
Winkle

(10) Patent No.: US 8,921,327 B2
(45) Date of Patent: Dec. 30, 2014

(54) ECTOPARASITICIDAL METHODS AND FORMULATIONS

(71) Applicant: Eli Lilly and Company, Indianapolis, IN (US)

(72) Inventor: Joseph Raymond Winkle, Carmel, IN (US)

(*) Notice: Subject to any disclaimer, the term of this patent is extended or adjusted under 35 U.S.C. 154(b) by 0 days.

(21) Appl. No.: 14/073,905

(22) Filed: Nov. 7, 2013

(65) Prior Publication Data

US 2014/0135280 A1 May 15, 2014

Related U.S. Application Data

(60) Provisional application No. 61/726,176, filed on Nov. 14, 2012.

(51) Int. Cl.
| | | |
|---|---|---|
| *A01N 43/22* | (2006.01) | |
| *A61K 47/10* | (2006.01) | |
| *A61K 9/00* | (2006.01) | |
| *A61K 47/22* | (2006.01) | |
| *A61K 31/704* | (2006.01) | |

(52) U.S. Cl.
CPC ............ *A01N 43/22* (2013.01); *A61K 47/10* (2013.01); *A61K 9/0017* (2013.01); *A61K 47/22* (2013.01); *A61K 31/704* (2013.01)
USPC .......................................................... 514/28

(58) Field of Classification Search
USPC .......................................................... 514/28
See application file for complete search history.

(56) References Cited

U.S. PATENT DOCUMENTS

| | | | |
|---|---|---|---|
| 6,001,981 A | 12/1999 | DeAmicis et al. | |
| 6,063,771 A | 5/2000 | Snyder | |
| 6,664,237 B1 | 12/2003 | Snyder | |
| 6,800,614 B2 | 10/2004 | Lewer et al. | |
| 6,927,210 B1 | 8/2005 | Thompson et al. | |
| 6,933,318 B1 | 8/2005 | Kassebaum et al. | |
| 7,030,095 B2 | 4/2006 | Ho et al. | |
| 7,683,161 B2 | 3/2010 | Podhorez et al. | |
| 8,178,500 B2 | 5/2012 | Qin et al. | |
| 2005/0032716 A1 | 2/2005 | Lowe et al. | |
| 2007/0104750 A1 | 5/2007 | Wilson et al. | |
| 2008/0108800 A1 | 5/2008 | Adaway et al. | |
| 2010/0286076 A1 | 11/2010 | Snyder et al. | |
| 2010/0324129 A1 | 12/2010 | Meyer et al. | |

FOREIGN PATENT DOCUMENTS

| | | |
|---|---|---|
| EP | 2248422 A1 | 11/2010 |
| WO | WO 01/11962 | 2/2001 |
| WO | WO 01/12156 | 2/2001 |
| WO | WO2008/096231 | 8/2008 |
| WO | WO 2009/030238 | 3/2009 |
| WO | WO 2010/030501 | 3/2010 |
| WO | WO 2010/023171 | 4/2010 |
| WO | WO 2010/129491 | 11/2010 |
| WO | 2010/148053 A1 | 12/2010 |

OTHER PUBLICATIONS

Dow AgroSciences Receives First Global Registration for Spinetoram Insecticide, Dow AgroSciences Newsroom, Corporate News, Aug. 10, 2007.
Dow AgroSciences Spinetoram Technical Bulletin, Nov. 2006.
Huang, Ke-Xue et al., "Recent Advances in the Biochemistry of Spinosyns", Applied Microbiology and Biotechnology, 82(1):13-23 (2009).
Kady et al., "Toxicity of Two Potential Bio-insecticides Against Moveable Stages of Tetranychusurticae Koch", Journal of Applied Sciences Research, 3(11):1315-1319 (2007).
Sparks et al., "Neural network-based QSAR and insecticide discovery spinetoram", Journal of Computer Aided Molecular Design, 22:393-401 (2008).
Beugnet, Frederic et al., "Insecticide and acaricide molecules and/or combinations to prevent pet infestation by ectoparasites" Trends in Parasitology, vol. 28, No. 7, Apr. 24, 2012 pp. 267-279, XP028493882, ISSN: 1471-4922, DIO: 10.1016/J.Pt. 2012.04.004 [retrieved on Apr. 24, 2014] p. 274, col. 1, last three paragraphs—col. 2, para. 2 (13 pages).
International Search Report and Written Opinion in PCT/US2013/068848, dated Apr. 29, 2014, 10 pages.

*Primary Examiner* — Kristin Vajda
(74) *Attorney, Agent, or Firm* — McAndrews, Held & Malloy, Ltd.

(57) ABSTRACT

Provided are novel methods and formulations for topically controlling ectoparasite infestations in animals using spinetoram, or a pharmaceutically acceptable salt thereof.

25 Claims, No Drawings

ECTOPARASITICIDAL METHODS AND FORMULATIONS

Ectoparasites such as fleas, lice, blowflies, mosquitoes, ticks and mites are problematic for man and animal alike. Such pests seriously impact productivity in the domesticated animal industry by reducing weight gain, causing poor quality hide, wool, and meat, and in some cases resulting in death. Ectoparasites also cause disease and discomfort in companion animals. Ectoparasites are known to carry bacteria and viruses which are pathogenic to humans. The diseases which ectoparasites cause include malaria, lymphatic filariasis, trachoma, trypanosomiasis, and river blindness, for example.

Efforts for controlling ectoparasites have included the use of insecticides and pesticides. For example, spinosyns, which are naturally derived fermentation products, have been employed as ectoparasiticides in animals and humans. (Snyder, U.S. Pat. No. 6,063,771 and U.S. Pat. No. 6,664,237; Kassebaum et al., U.S. Pat. No. 6,933,318; and Janssen et al., U.S. Pat. No. 7,030,095).

Derivatives of spinosyns have been employed in agricultural applications. (DeAmicis et al., U.S. Pat. No. 6,001,981). Spinetoram is the common name for a mixture of 25-90%, preferably 50-90% (2R,3aR,5aR,5bS,9S,13S,14R,16a5, 16bR)-2-(6-deoxy-3-O-ethyl-2,4-di-O-methy-1-.alpha.-L-mannopyranosyloxy)-13-[(2R,5S,6R)-5-(dimethylamino)tetrahydro-6-methylpyran-2-yloxy]-9-ethyl-2,3,3a,4,5,5a,5b,6,9,10,11,12,13,14,16a,16b-hexadecahydro-14-methyl-1H-as-indaceno[3,2-d]oxacyclododecine-7,15-dione (referred to as "dihydro-Et-J", formula I below), and 10-75%, preferably 10-50% (2R,3aR,5aS,5bS,9S,13S,14R,16aS, 16bS)-2-(6-deoxy-3-O-ethyl-2,4-di-O-methy-1-.alpha.-L-mannopyranosyloxy)-13-[(2R,5S,6R)-5-(dimethylamino)tetrahydro-6-methylpyran-2-yloxy]-9-ethyl-2,3,3a,5a,5b,6,9,10,11,12,13,14,16a,16b-tet-radecahydro-4,14-dimethyl-1H-as-indaceno[3,2-o]oxacyclododecine-7,15-dione (referred to as "Et-L", formula 11 below).

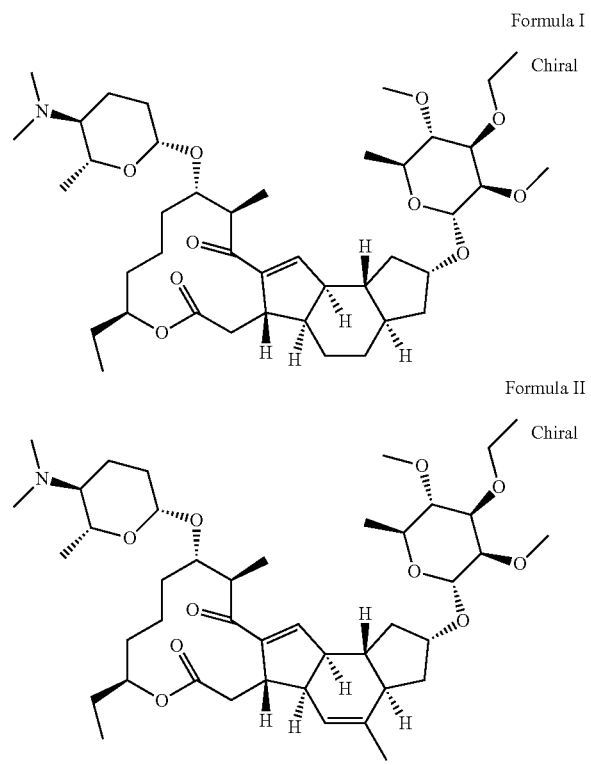

(Podhorez et al., U.S. 2008/0108800A1). Spinetoram is described as providing long-lasting control of a broad spectrum of insect pests in a variety of crops (Dow AgroSciences Spinetoram Technical Bulletin, November 2006). It has been reported spinetoram has been registered in New Zealand as an insecticide in the pome fruit market ("Dow AgroSciences Receives First Global Registration for Spinetoram Insecticide," Dow AgroSciences Newsroom, Corporate News, Aug. 10, 2007).

Spinetoram has been developed and commercialized as a topical flea control product in the USA, and is marketed under the trade name Assurity™. Assurity received authorization for marketing in November 2010. The formulation of Assurity contains, in % w/w: 39.6% of spinetoram (210 mg), about 54% benzyl alcohol, about 0.1% of butylated hydroxytoluene, and about 0.1% of citric acid.

While the use of spinosyns and other insecticides and pesticides have been beneficial, alternative or improved formulations and methods are needed. Desirable formulations and methods would not only provide alternative therapies, but would also overcome one or more limitations of current therapies. Such limitations include toxicity, safety, efficacy (potency and duration), resistance, and side effect issues. One such benefit is reducing the amount of active ingredient used and thus also reducing the amount of active ingredient exposed to the environment and target animal. Also impacting the beneficial use of insecticides and pesticides are administration obstacles, which include mode and recurrence of administration, as well as undesirable side effects, such as irritation or hair loss. For example, reducing the frequency of administration while maintaining efficacy is desirable, as dosing animals is often inconvenient and/or difficult.

The present invention encompasses ectoparasiticidal methods and formulations, particularly for use in cats, which provide alternative options for combating ectoparasiticite infestations. Further, the formulations of the present invention overcome one or more limitations in the use of current insecticides and pesticides, particularly in providing efficacious, long term, safe, topical control of ectoparasites. The invention provides excellent speed-of-kill and residual efficacies.

The invention provides methods of controlling ectoparasite infestations of a cat by topically administering an effective amount of spinetoram, or a pharmaceutically acceptable salt thereof, to the cat. The invention also provides pharmaceutical formulations for topically controlling ectoparasite infestations using spinetoram, or a pharmaceutically acceptable salt thereof, and a pharmaceutically acceptable carrier. The invention also provides methods for controlling flea infestations of a cat by topically administering an effective amount of spinetoram or a pharmaceutically acceptable salt thereof to said cat. Another aspect of the methods and formulations using spinetoram is the ability to provide long term topical control of ectoparasite infestations, thus decreasing the recurrence of dosing an animal, such as no more than every one or two weeks, or every month or more, as well as initial knockdown efficacy.

The term "cat" includes *Felis catus* and *Felis silvestris catus*. While the inventions may be used with a cat of any age, the cat preferably is eight weeks or older. Mature cats generally weigh from 2.5 to 6 kg, while kittens generally weigh 0.7 to 1.2 kg.

Ectoparasites include insect and acarine pests which commonly infest or infect cats, and include the egg, larval, pupal, nymphal, and adult stages thereof. Such pests include fleas, lice, mosquitoes, mites, ticks, and blood-sucking, biting or nuisance fly species. A particular target is fleas, and more particularly *Ctenocephalides felis*, wherever located in the world, including those found in Europe.

"Controlling" refers to either ameliorating or eliminating a current infestation, or preventing an infestation, in a cat.

"Topically" is defined as applying to the outside surface area of cat, and includes the skin or hair. Preferably, topically is not a non-trivial systemic, such as transdermal, application.

"Effective amount" refers to the amount of spinetoram, or a pharmaceutically acceptable salt thereof, sufficient to control an ectoparasite, and includes causing a measurable reduction in the ectoparasite infestation population. This control may be the result of spinetoram or its conjugate or pharmaceutically acceptable salt entering the system of the pest when it feeds, or through a repellant action due to the presence of spinetoram or its conjugate or salt thereof.

"Pharmaceutically acceptable" as used in this application, for example with reference to salts and formulation components such as carriers and ingredients, includes "veterinary acceptable" and "dermatological acceptable".

Pharmaceutically acceptable salts and common methodology for preparing them are known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol. 66, No. 1, January 1977.

The term "about" when used with amounts, is to be read as including the amount(s) specified, and amounts within ±2% of the amount(s).

The term "carrier" is used herein to describe any ingredient other than the active components in a formulation. The choice of carrier will to a large extent depend on factors such as the particular mode of administration, the effect of the carrier on solubility and stability, and the nature of the dosage form. As such, the present formulations can also contain other optional ingredients, such as: antioxidants, buffering agents, preservatives, surfactants, chelating agents, humectants, miscibilizing agents, UV-absorbing compounds or photostabilizers, viscosity-modifying agents, antimicrobial agents, dyes, perfumes, conditioners, deodorants and physiologically or dermatological acceptable diluents, excipients or adjuvants. Such agents are known in the art.

Spinetoram and its salts may be formulated as liquid pharmaceutical compositions for topical administration, and preferably in unit dose form. The pharmaceutical formulations of this invention include benzyl alcohol and propylene carbonate. The composition in one aspect contains about 70-100 mg of spinetoram. In another aspect, the composition contains about 85-95 mg of spinetoram. In another aspect, the composition contains about 91 mg of spinetoram, or a pharmaceutically acceptable salt thereof.

The term "unit dose" or "unit dosage" form means physically discrete units suitable as unitary dosages for administration, each unit containing a predetermined quantity of active material calculated to produce the desired therapeutic effect, in association with one or more pharmaceutically acceptable carriers.

In one aspect of the invention, the wt % of spinetoram, or a pharmaceutically acceptable salt thereof, in the formulation is about 8-14 wt/wt %. In another aspect of the invention, the wt % of spinetoram, or a pharmaceutically acceptable salt thereof, in the formulation is about 10-12 wt/wt %. In another aspect of the invention, the wt % of spinetoram, or a pharmaceutically acceptable salt thereof, in the formulation is about 11.2 wt/wt %. Preferably, the total amount of the formulation is about 0.7 mL.

In one aspect of the invention, the amount of benzyl alcohol is about 15-20 wt % of the formulation. In another aspect of the invention, the amount of benzyl alcohol is about 17-19 wt % of the formulation. In another aspect of the invention, the amount of benzyl alcohol is about 18 wt % of the formulation. Preferably, the total amount of the formulation is about 0.7 mL.

In one aspect of the invention, the amount of propylene carbonate is about 65-75 wt % of the formulation. In another aspect of the invention, the amount of propylene carbonate is about 67-71 wt % of the formulation. In another aspect of the invention, the amount of propylene carbonate is about 69 wt % of the formulation. Preferably, the total amount of the formulation is about 0.7 mL.

In one aspect of the invention, the range for spinetoram, or a pharmaceutically acceptable salt thereof, is from about 11-142 mg/kg weight of the target animal. In another aspect of the invention, the range for spinetoram, or a pharmaceutically acceptable salt thereof, is from about 14-135 mg/kg weight of the target animal. In another aspect of the invention, the range for spinetoram, or a pharmaceutically acceptable salt thereof, is from about 15-130 mg/kg weight of the target animal.

In one aspect of the invention, the formulation is a topical liquid pharmaceutical formulation comprising about 8-14 wt/wt % of spinetoram, or a pharmaceutically acceptable salt thereof, about 15-20 wt/wt % of benzyl alcohol, and about 65-75 wt/wt % of propylene carbonate, and optionally one or more pharmaceutically acceptable carriers. Preferably, the total amount of this formulation is about 0.7 mL.

In one aspect of the invention, the formulation is a topical liquid pharmaceutical formulation comprising about 11.2 wt/wt % of spinetoram, about 18 wt/wt % of benzyl alcohol, and about 69 wt/wt % of propylene carbonate, and optionally one or more pharmaceutically acceptable carriers. Preferably, the total amount of this formulation is about 0.7 mL.

Administration of spinetoram or a salt thereof may be topically administered by any suitable application. The compound and formulations can be administered topically to an animal by the direct laying on or spreading of the composition on the skin or hair. Preferably, the formulation is applied at the base of the skull. Formulations can be applied by spot-on application, plunge or spray dipping, jetting with a hand held spray or in a race, or as a back-line spray or pour-on. The administration can occur daily, weekly, biweekly, or monthly, depending on the severity of the infestation and exposure to the pest, for instance. While monthly administration is normally preferred in most situations, it should be understood sufficient residual efficacy after dosing extends 5, 6, 7, 8, or 9 weeks or more in some instances.

The following formulation is tested for speed to kill, residual efficacy, and side effect profile.

Formulation 1

Formulation Specific Gravity: 1.16

| | |
|---|---|
| Spinetoram: | 11.2 wt/wt % (91 mg) |
| Benzyl alcohol | 18.0 wt/wt % |
| Propylene carbonate | ~69 wt/wt % |
| Butylated hydroxytoluene | 0.1 wt/wt % |
| Citric acid | 0.1 wt/wt % |

A residual flea speed-of-kill study is conducted on cats to illustrate Formulation I begins killing within 30 minutes and that it reaches 90% kill within 8 hours on fleas. As seen in Table 1, Formulation 1 meets the criteria on day one of administration for both killing within 30 minutes as well as being greater than 90% kill at 8 hours. After 4 weeks, approximately 97% kill is still achieved within 12 hours.

TABLE 1

| Measured Parameter | Speed of Kill Study | | | | |
|---|---|---|---|---|---|
| | 30 min | 4 hours | 8 hours | 12 hours | 24 hours |
| | Day 0 | | | | |
| Arithmetic Mean % Efficacy | 14.38 | 15.64 | 91.04 | 100 | — |
| Geometric Mean % Efficacy | 14.55 | 20.10 | 95.29 | 100 | — |
| Median (Live Flea Count) | 66.5 | 66.5 | 4.5 | 0.0 | — |
| Min, Max (Live Flea Count) | 45, 100 | 31, 89 | 0, 14 | 0, 0 | — |
| ±Std. Dev. | 20.38 | 23.28 | 6.36 | 0.00 | — |
| | Day 7 | | | | |
| Arithmetic Mean % Efficacy | 52.52 | 95.89 | 99.78 | 100 | — |
| Geometric Mean % Efficacy | 55.32 | 97.61 | 99.84 | 100 | — |
| Median (Live Flea Count) | 35.5 | 2.5 | 0.0 | 0.0 | — |
| Min, Max (Live Flea Count) | 21, 64 | 0, 12 | 0, 1 | 0, 0 | — |
| ±Std. Dev. | 16.31 | 4.50 | 0.41 | 0.00 | — |
| | Day 14 | | | | |
| Arithmetic Mean % Efficacy | 23.69 | 79.36 | 86.65 | 96.01 | — |
| Geometric Mean % Efficacy | 25.84 | 80.54 | 91.16 | 97.66 | — |
| Median (Live Flea Count) | 66.0 | 14.0 | 6.5 | 1.5 | — |
| Min, Max (Live Flea Count) | 32, 72 | 11, 32 | 1, 28 | 0, 10 | — |
| ±Std. Dev. | 15.07 | 7.91 | 10.41 | 3.82 | — |
| | Days 21-22 | | | | |
| Arithmetic Mean % Efficacy | — | 59.65 | 89.80 | 92.55 | 98.80 |
| Geometric Mean % Efficacy | — | 61.47 | 93.42 | 94.83 | 99.10 |
| Median (Live Flea Count) | — | 29.5 | 4.5 | 4.0 | 0.5 |
| Min, Max (Live Flea Count) | — | 14, 48 | 1, 18 | 0, 14 | 0, 2 |
| ±Std. Dev. | — | 11.88 | 7.56 | 4.96 | 0.98 |
| | Days 28-29 | | | | |
| Arithmetic Mean % Efficacy | — | 36.05 | 78.63 | 90.43 | 94.55 |
| Geometric Mean % Efficacy | — | 40.47 | 89.47 | 95.48 | 96.72 |
| Median (Live Flea Count) | — | 44.5 | 8.5 | 4.5 | 3.0 |
| Min, Max (Live Flea Count) | — | 21, 66 | 0, 46 | 0, 23 | 0, 11 |
| ±Std. Dev. | — | 18.10 | 18.30 | 8.81 | 4.22 |

Residual activity of Formulation 1 is tested twice. Results are shown in Table 2. Outstanding efficacy is illustrated through Day 30 and Day 37.

TABLE 2

| Measured Parameter | Day 2 | Day 9 | Day 16 | Day 23 | Day 30 | Day 37 |
|---|---|---|---|---|---|---|
| | Residual Study I | | | | | |
| Arithmetic Mean % Efficacy | 100 | 100 | 100 | 99.39 | 97.10 | 89.56 |
| Geometric Mean % Efficacy | 100 | 100 | 100 | 99.67 | 98.05 | 96.01 |
| Median (Life Flea Count) | 0.0 | 0.0 | 0.0 | 0.0 | 1.5 | 1.5 |
| Min, Max (# Live Fleas) | 0, 0 | 0, 0 | 0, 0 | 0, 3 | 0, 6 | 0, 28 |
| Mean (SD) | 0.00 (0.00) | 0.00 (0.00) | 0.00 (0.00) | 0.38 (1.06) | 2.13 (2.30) | 7.13 (10.16) |
| | Residual Study II | | | | | |
| Arithmetic Mean % Efficacy | 100 | 100 | 100 | 99.04 | 99.79 | 96.73 |
| Geometric Mean % Efficacy | 100 | 100 | 100 | 99.37 | 99.84 | 97.85 |
| Median (Life Flea Count) | 0.0 | 0.0 | 0.0 | 0.0 | 0.0 | 1.5 |

TABLE 2-continued

| Measured Parameter | Day 2 | Day 9 | Day 16 | Day 23 | Day 30 | Day 37 |
|---|---|---|---|---|---|---|
| Min, Max (# Live Fleas) | 0, 0 | 0, 0 | 0, 0 | 0, 1 | 0, 1 | 0, 7 |
| Mean (SD) | 0.00 (0.00) | 0.00 (0.00) | 0.00 (0.00) | 0.75 (1.16) | 0.13 (0.35) | 2.00 (2.45) |

A study is conducted to evaluate the safety and side effect profile of Formula 1 on cats. Formulation 1 is well tolerated in cats, particularly in that there is no or little hair loss observed.

The studies illustrate that the desired efficacy and side effect profile is provided by the invention. As the amount of spinetoram used in the invention is lower than what is commercially available, the exposure of the environment and the target animal to the active ingredient is reduced. Additionally, the invention's solvent system provided the desired safety and side effect profile while other solvents/solvent systems failed to do so.

I claim:

1. A topical liquid pharmaceutical formulation comprising about 8-14 wt/wt % of spinetoram, or a pharmaceutically acceptable salt thereof, about 15-20 wt/wt % of benzyl alcohol, and about 65-75 wt/wt % of propylene carbonate, and optionally one or more pharmaceutically acceptable carriers.

2. The formulation of claim 1, wherein said spinetoram, or a pharmaceutically acceptable salt thereof, is present in an amount of about 70-100 milligrams.

3. The formulation of claim 2, wherein said spinetoram, or a pharmaceutically acceptable salt thereof, is present in an amount of about 85-95 milligrams.

4. The formulation of claim 3, wherein said spinetoram, or a pharmaceutically acceptable salt thereof, is present in an amount of about 91 milligrams.

5. The formulation of claim 1, wherein said spinetoram, or a pharmaceutically acceptable salt thereof, is present in an amount of about 10-12 wt/wt % of the formulation.

6. The formulation of claim 5, wherein said spinetoram, or a pharmaceutically acceptable salt thereof, is present in an amount of about 11.2 wt/wt %.

7. The formulation of claim 1, wherein said benzyl alcohol is present in an amount of about 17-19 wt/wt %.

8. The formulation of claim 7, wherein said benzyl alcohol is present in an amount of about 18 wt/wt %.

9. The formulation of claim 1, wherein said propylene carbonate is present in an amount of about 67-71 wt/wt %.

10. The formulation of claim 9, wherein said propylene carbonate is present in an amount of about 69 wt/wt %.

11. The formulation of claim 1, wherein said pharmaceutical formulation has a volume of about 0.7 ml.

12. The formulation of claim 1, wherein said formulation is unit dosage form.

13. A topical liquid pharmaceutical formulation comprising about 11.2 wt/wt % of spinetoram, about 18 wt/wt % of benzyl alcohol, and about 69 wt/wt % of propylene carbonate, and optionally one or more pharmaceutically acceptable carriers.

14. The formulation of claim 13, wherein said formulation has a volume of about 0.7 ml.

15. The formulation of claim 13, wherein said formulation is in unit dosage form.

16. A method of controlling an ectoparasite infestation on a cat which comprises topically administering a formulation of claim 1 on said cat.

17. The method of claim 16, wherein said administration is spot-on, plunge or spray dipping, jetting with a hand held spray or in a race, or as a back-line spray or pour-on.

18. The method of claim 16, wherein said administration is carried out no more than biweekly.

19. The method of claim 18, wherein said administration is carried out no more than monthly.

20. The method of claim 16, wherein said ectoparasite is *Ctenocephalides felis*.

21. A method of controlling an ectoparasite infestation on a cat which comprises topically administering a formulation of claim 13 on said cat.

22. The method of claim 21, wherein said administration is spot-on, plunge or spray dipping, jetting with a hand held spray or in a race, or as a back-line spray or pour-on.

23. The method of claim 21, wherein said administration is carried out no more than biweekly.

24. The method of claim 23, wherein said administration is carried out no more than monthly.

25. The method of claim 21, wherein said ectoparasite is *Ctenocephalides felis*.

* * * * *